United States Patent [19]

Edwards

[11] 4,219,648
[45] Aug. 26, 1980

[54] 7-[[AMINO(1,3-DIHYDROBENZO[C]-THIENYL)ACETYL]AMINO]CEPHALOSPORIN DERIVATIVES

[75] Inventor: Michael L. Edwards, Cincinnati, Ohio

[73] Assignee: Richardson-Merrell Inc., Wilton, Conn.

[21] Appl. No.: 883,409

[22] Filed: Mar. 6, 1978

[51] Int. Cl.$^2$ .................. C07D 501/36; C07D 501/34
[52] U.S. Cl. ........................................ 544/21; 544/27; 544/28; 424/246
[58] Field of Search .............................. 544/28, 21, 27

[56] References Cited

U.S. PATENT DOCUMENTS

| | | | |
|---|---|---|---|
| 3,134,774 | 5/1964 | Chow et al. | 544/25 |
| 3,989,694 | 11/1976 | Berges | 544/27 |
| 4,000,133 | 12/1976 | Kariyone et al. | 544/27 |
| 4,020,060 | 4/1977 | Erickson et al. | 424/246 |
| 4,033,956 | 7/1977 | Erickson et al. | 424/246 |

FOREIGN PATENT DOCUMENTS 1906194  9/1969  Fed. Rep. of Germany.

OTHER PUBLICATIONS

Sienko et al., Chemistry, (1966), pp. 19–20.
Chauvette et al., "Antimicrobial Agents", Chemotherapy (1962), pp. 687–694.
Sassiver et al., Ibid., (1968), pp. 101–108.

Primary Examiner—Donald G. Daus
Assistant Examiner—David E. Wheeler
Attorney, Agent, or Firm—William J. Stein; Eugene O. Retter; George W. Rauchfuss, Jr.

[57] ABSTRACT

This invention is directed to new 7-[[amino(1,3-dihydrobenzo[c]thien-5-yl)acetyl]amino]cephalosporin derivatives useful as antibiotics.

24 Claims, No Drawings

7-[[AMINO(1,3-DIHYDROBENZO[c]THIENYL-)ACETYL]AMINO]CEPHALOSPORIN DERIVATIVES

BACKGROUND OF THE INVENTION

1. Field of the Invention

This invention relates to new and useful cephalosporin compounds and processes for preparing them.

2. Prior Art

A search of the prior art uncovered U.S. Pat. Nos. 3,577,412 and 3,790,565 which disclose 7-(α- or β-substitutedbenzothienyl)acetamido or 7-(α- or β-substitutedbenzothienyl)carboxamido cephalosporin derivatives. These references do not describe or suggest the compounds of this invention.

SUMMARY OF THE INVENTION

Compounds of the general formula I are useful as antibiotics

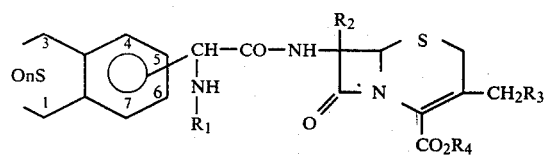

General Formula 1 wherein n is 0, 1 or 2; substitution on the 1,3-dihydrobenzo[c]thiophene ring occurs at position 4 or 5; $R_1$ is hydrogen, a straight or branched lower alkanoyl group which has from 2 to 5 carbon atoms, or a straight or branched lower alkoxycarbonyl group in which the alkoxy portion has from 1 to 4 carbon atoms; $R_2$ is hydrogen or methoxy; $R_3$ is hydrogen, a straighr or branched lower alkanoyloxy group having 2 to 5 carbon atoms, 1,3,4-thiadiazol-2-ylthio; 5-methyl-1,3,4-thiadiazol-2-ylthio; tetrazol-5-ylthio; 1-methyltetrazol-5-ylthio; 1,3,4-oxadiazol-2-ylthio; 5-methyl-1,3,4-oxadiazol-2-ylthio; 1,3,4-triazol-2-ylthio; 5-methyl-1,3,4-triazol-2-ylthio or 1,2,3-triazol-5-ylthio; $R_4$ is hydrogen, a straight or branched lower alkyl group of from 1 to 4 carbon atoms, an alkanoyloxymethyl group in which the alkanoyl portion is straight or branched and has from 2 to 5 carbon atoms, an alkanoylaminomethyl group in which the alkanoyl portion is straight or branched and has from 2 to 5 carbon atoms and the amine nitrogen may be substituted with a straight or branched lower alkyl group having 1 to 4 carbon atoms, a p-(alkanoyloxy)benzyl group in which the alkanoyl portion is straight or branched and has from 2 to 5 carbon atoms, an aminoalkanoyloxymethyl group in which the alkanoyl portion has from 2 to 15 carbon atoms and the amino nitrogen may be mono- or disubstituted with a straight or branched lower alkyl group having from 1 to 4 carbon atoms, and optical isomers thereof, or a pharmaceutically acceptable salt thereof.

DETAILED DESCRIPTION

In the general formula 1 the groups represented by $R_1$ in addition to hydrogen may also be an alkanoyl group as represented by the structure

wherein $R_5$ is selected from a straight or branched lower alkyl group which has from 1 to 4 carbon atoms. Additionally, $R_1$ may be an alkoxycarbonyl group as represented by the structure

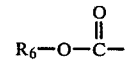

wherein $R_6$ is selected from a straight or branched lower alkyl group which has from 1 to 4 carbon atoms. Representative lower alkyl groups for $R_5$ and $R_6$ are methyl, ethyl, n-propyl, isopropyl, n-butyl, isobutyl and tert-butyl. The preferred group for $R_1$ as shown in general formula 1 is hydrogen.

The groups represented by $R_2$ in general formula 1 are either hydrogen or methoxy; hydrogen being the more preferred.

In the general formula 1, $R_3$ in addition to hydrogen may be an alkanoyloxy group as represented by the structure

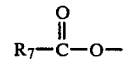

wherein $R_7$ is a straight or branched lower alkyl group of from 1 to 4 carbon atoms.

Additionally, $R_3$ in general formula 1 may be 1,3,4-thiadiazol-2-ylthio; 5-methyl-1,3,4-thiadiazol-2-ylthio; tetrazol-5-ylthio; 1-methyltetrazol-5-ylthio; 1,3,4-oxadiazol-2-ylthio; 5-methyl-1,3,4-oxadiazol-2-ylthio; 1,3,4-triazol-2-ylthio; 5-methyl-1,3,4-triazol-2-ylthio and 1,2,3-triazol-5-ylthio; the respective structures of these groups are shown below.

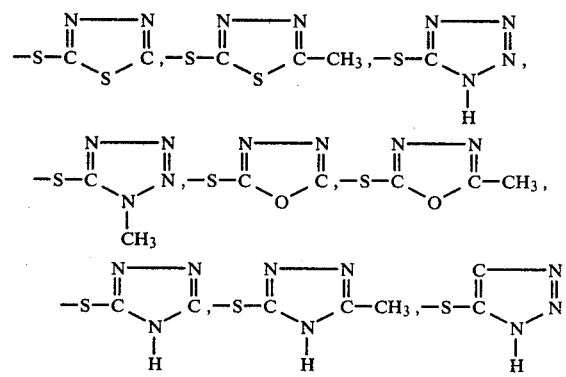

The preferred groups for $R_3$ as shown in general formula 1 are hydrogen, acetyloxy and 5-methyl-1,3,4-thiadiazol-2-ylthio.

In general formula 1, $R_4$ may be hydrogen or a straight or branched lower alkyl group of from 1 to 4 carbon atoms; or $R_4$ may represent an alkanoyloxymethyl group as represented by the structure

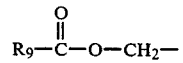

in which $R_9$ is selected from a straight or branched lower alkyl group of from 1 to 4 carbon atoms.

In general formula 1, $R_4$ may represent an alkanoylaminomethyl group as represented by the structure

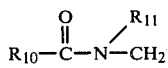

in which $R_{10}$ is selected from a straight or branched lower alkyl group which has from 1 to 4 carbon atoms or a straight or branched alkoxy group of from 1 to 4 carbon atoms and $R_{11}$ is hydrogen or a straight or branched lower alkyl group which has from 1 to 4 carbon atoms.

In general formula 1, $R_4$ may also represent a p-(alkanoyloxy()benzyl group as represented by the structure

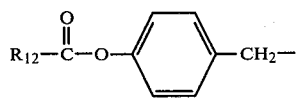

in which $R_{12}$ is a straight or branched lower alkyl group of from 1 to 4 carbon atoms. Additionally $R_4$, in general formula 1, may represent an aminoalkanoyloxymethyl group as represented by the structure

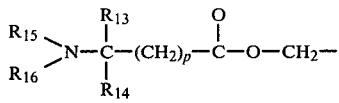

in which p has a value of from 0 to 5, $R_{13}$ and $R_{14}$ are selected from hydrogen or a straight or branched lower alkyl group of from 1 to 4 carbon atoms and $R_{15}$ and $R_{16}$ are selected from hydrogen or a straight or branched lower alkyl group of from 1 to 4 carbon atoms.

Illustrative examples of the straight or branched lower alkyl groups of from 1 to 4 carbon atoms are: methyl, ethyl, n-propyl, isopropyl, n-butyl, isobutyl and tert-butyl.

It is obvious that compounds of general formula 1 exist as optical isomers. These optical isomers are deemed part of this invention.

It is also obvious that cis and trans compounds of general formula 1 exist as a result of the spatial arrangement at positions 6 and 7. The cis arrangement for $R_2$ with respect to the substituent at the 6-position is preferred.

Non-toxic acid addition salts formed by the reaction of organic and inorganic acids with compounds generally described by general formula 1 are within the scope of this invention. Acids which may be used and which are classified as inorganic acids are illustrated by the following: hydrogen chloride, hydrogen bromide, hydrogen iodide, sulfuric acid, orthio-, meta- and pyrophosphoric acid, and sulfamic acid. Organic acids which may be used to form addition salts with compounds represented by formula 1 are illustrated by the following: maleic, acetic, citric, oxalic, succinic, benzoic, tartaric, fumaric, malic, mandelic and ascorbic acid.

Non-toxic salts formed by the reaction of organic and inorganic bases with compounds generally described by general formula 1 are within the scope of this invention. Bases which may be used and which are classified as inorganic are sodium hydroxide, potassium carbonate, calcium oxide, magnesium hydroxide and ammonium hydroxide. Bases which may be classified as organic include the primary, secondary and tertiary amines such as cyclohexylamine, dibutylamine, trioctylamine and pyridine.

The compounds of this invention may be administered in a manner similar to that employed in the administration of other well known cephalosporins such as cephalexin, cephaloridine and cephaloglycin. The compounds of this invention may be administered alone or in a pharmaceutical composition. The cephalosporin derivatives described herein may be administered orally, parenterally and topically to warm blooded animals such as birds and mammals. Illustrative of the mammals to which these cephalosporin derivatives may be administered are cats, dogs, cattle, horses and humans.

The compounds described herein may be administered orally in the form of tablets, capsules or pills and in the form of elixirs and suspensions.

The compounds described herein may be administered parenterally in the form of a sterile solution which may contain other solutes such as saline or glucose so as to make the solutions isotonic. For topical administration the compounds may be in a cream, an ointment, a topical solution or a foam.

Illustrative of the bacteria against which these compounds are effective are *Staphylococcus aureus*, *Salmonella schottmuelleri*, *Klebsiella pneumoniae*, *Diplococcus pneumoniae* and *Streptococcus pyogenes*.

Illustrative examples of compounds of this invention are set forth below. Other compounds are described hereinafter.

3-[(acetyloxy)methyl]-7-[[amino(1,3-dihydrobenzo[c]-thien-5-yl)acetyl]amino]-8-oxo-5-thia-1-azabicyclo[4.2.0]oct-2-ene-2-carboxylic acid $S^2,S^2$-dioxide, 7-[[amino(1,3-dihydrobenzo[c]thien-5-yl)acetyl]amino]-3-methyl-8-oxo-5-thia-1-azabicyclo[4.2.0]oct-2-ene-2-carboxylic acid $S^2,S^2$-dioxide, and 7-[[amino(1,3-dihydrobenzo[c]thien-5-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid $S^2,S^2$-dioxide.

Compounds of general formula 1 may be prepared by reacting a compound of formula 2

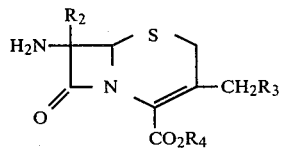

Formula 2 with a compound of formula 3

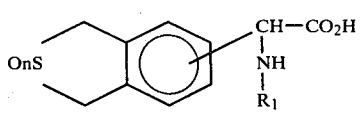

Formula 3 or a functional equivalent thereof wherein $R_1$, $R_2$, $R_3$, $R_4$, n and the substitution of the 1,3-dihydrobenzo[c]thiophene are as defined in general formula 1 with the proviso that $R_1$ is other than hydrogen. Optionally, the coupling reaction may be run in the presence of a coupling agent such as N-ethoxycarbonyl-2-ethoxy-1,2-dihydroquinoline (EEDQ) provided that $R_1$ and $R_4$ are other than hydrogen. Optionally, the coupling reaction may be run in the presence of a dehydrating agent such as a carbodiimide for example, dicyclohexylcarbodiimide. When $R_1$ and $R_4$ are groups other than hydrogen in the coupled product, these groups may be hydrolyzed using the general procedure described in U.S. Pat. No. 3,657,232.

Functional derivatives of the acid include the acid halide, for example, the acid chloride, acid anhydrides, including the mixed anhydrides with, for example, alkyl phosphoric acid, lower aliphatic monoesters of carbonic acid or alkyl or aryl sulfonic acids.

The coupling reaction is usually carried out in the presence of a solvent. Suitable solvents include ethyl acetate, acetone, tetrahydrofuran, dioxane, acetonitrile, chloroform, ethylene chloride, benzene and benzene-ethanol mixtures. Additionally, hydrophilic solvents can be used alone or admixed with water. The coupling reaction may be carried out in the presence of a base, for example, triethylamine or an alkaline bicarbonate. Temperatures of the reaction vary from about $-10°$ C. to about 100° C. and the reaction times vary from about 0.5 to about 24 hours. The coupled products are isolated by conventional techniques.

For example, compounds as defined in formulas 2 and 3, with n, $R_1$, $R_2$, $R_3$ and $R_4$ having the meanings defined for formula 1 with substitution at position 4 or 5 in the 1,3-dihydrobenzo[c]thiophene system may be coupled according to the general method of Belleau, et al., J. Am. Chem. Soc., 90, 1651 (1968) with the proviso that $R_1$ is other than hydrogen and $R_4$ is other than hydrogen. Equivalent amounts of a compound of formula 2, a compound of formula 3 and EEDQ are reacted in a solvent such as benzene, ethanol, tetrahydrofuran (THF) or ethyl acetate at a temperature from about 15° C. to about 90° C. for from 1 hour to about 12 hours. The product is recovered by conventional means.

Illustratively, coupling may be achieved by using the general procedure described by Spencer in J. Med. Chem., 9, 746 (1966). One equivalent of an acid, as represented by compounds of formula 3, $R_1$ other than hydrogen, is reacted with an alkyl chloroformate, for example, isobutylchloroformate at about $-10°$ C. to $+10°$ C. for from 0.5 to 2 hours in a solvent which contains an acid acceptor such as triethylamine. One equivalent of the amine of formula 2, which is to be coupled is added and the temperature is increased from about $-10°$ C. to about 20° C. for about 30 minutes to 3 hours. The coupled product is recovered by conventional means.

Illustratively, acid chlorides may be prepared from compounds of formula 3, $R_1$ is other than hydrogen, by reacting acid compound (0.1 mole) with thionyl chloride (0.11 mole) at 10° to 100° C. for from 0.5 hour to 10 hours. The acid chloride so formed is then reacted with an amine as represented by a compound of formula 2, in a solvent such as benzene, tetrahydrofuran or ethyl acetate in the presence of a base such as triethylamine or an alkaline bicarbonate at 10° C. to 90° C. for from 0.5 hour to 10 hours. The coupled product is then recovered by conventional means. The acid salt of the compound of formula 3 wherein $R_1$ is hydrogen, for example, the hydrochloride or the hydrobromide, may be converted to the acid chloride and then coupled with amine compounds of formula 2 as described above.

For example, the coupling of compounds represented by formula 2, with compounds represented by formula 3 wherein $R_1$ is other than hydrogen may be achieved using the general procedure described in U.S. Pat. No. 3,252,973. The compound of formula 3, 1 to 3 equivalents, is added to water and the pH adjusted to between 6.7–7.5. One equivalent of a compound of formula 2 and 1 to 2 equivalents of a carbodiimide, for example, dicyclohexylcarbodiimide or diisopropylcarbodiimide, in a solvent such as dioxane is added to the aqueous solution. After about 1 to 18 hours at a temperature from about 0° C. to about 20° C., the coupled compound is recovered by conventional means.

Compounds of formula 2 wherein $R_2$ is hydrogen, $R_3$ is hydrogen or acetyloxy and $R_4$ is hydrogen or a cation are commercially available or may be prepared by methods well known in the art. The corresponding compounds wherein $R_2$ is methoxy, $R_3$ is hydrogen or acetyloxy and $R_4$ is hydrogen can be prepared according to the procedure described in U.S. Pat. No. 3,778,432.

Compounds of formula 2 wherein $R_3$ is a heterocyclic thio group may be prepared by reacting a compound of formula 2, wherein $R_2$ is hydrogen or methoxy, $R_3$ is acetyloxy and $R_4$ is hydrogen, either as the acid or salt, e.g., the sodium salt, in about 500 ml to 2000 ml of a solvent such as water, acetone-water, or THF-water at a temperature of 30° C. to 90° C. under a nitrogen atmosphere and subsequently adding 1 equivalent of a base, such as, triethylamine or sodium bicarbonate, and 1 to 3 equivalents of heterocyclic thiol group as previously defined for $R_3$, general formula 1. This reaction mixture is heated at 30° to 90° C. for 2 to 6 hours after which the solvent is evaporated. The product is recovered from the reaction mixture by conventional means.

In a similar manner the heterocyclic thiol may be introduced into the coupled cephalosporin compound as represented by formula 1, $R_3$ is acetyloxy using the general procedure described in J. Antibiotics, 23, 131 (1970). This procedure may be used to prepare derivatives of formula 1 wherein $R_3$ is a heterocyclic thio group as previously defined for general formula 1.

Compounds of general formulas 1 and 2 wherein $R_4$ is an alkanoyloxymethyl group are prepared by reacting the corresponding acid in the form of a salt such as an alkali metal salt or a triethylammonium salt with an alkanoyloxymethyl halide of the structure

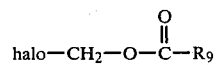

wherein halo is bromine or chlorine and the alkanoyl portion is straight or branched and has from 2 to 5 carbon atoms, as taught by the general procedure in U.S. Pat. No. 3,655,658.

Compounds of general formulas 1 and 2 wherein $R_4$ is alkanoylaminoethyl or alkoxycarbonylaminoethyl are prepared by treating a salt, for example, the alkali metal salt or the triethylammonium salt of acid derivatives of general formula 1. For example, the sodium salt is treated in an organic solent such as dimethylformamide or hexamethylphosphoramide at 10° to 30° C. with an equivalent amount of an alkanoylaminomethyl halide or an alkoxycarbonylaminoethyl halide for ½ to 3 hours after which the mixture is poured into ice water. The resulting precipitated product is isolated by standard procedures.

Compounds of general formulas 1 and 2 wherein $R_4$ is p-(alkanoyloxy)benzyl are prepared by adding 2 equivalents of the p-(alkanoyloxy)benzyl alcohol to a suspension of a salt, for example, the alkali metal salts or triethylammonium salts of acid derivatives of general formula 1. For example, the sodium salt is suspended in dimethylformamide or hexamethylphosphoramide after which the mixture is cooled to 0° C. 1.2 Equivalents of a carbodiimide, for example, dicyclohexylcarbodiimide, in dimethylformamide is added dropwise to the mixture with stirring. The mixture is stirred at 0° C. for ½ to 3 hours and then an additional 2 to 5 hours at room temperature. The formed dicyclohexylurea is removed by filtration and the filtrates is diluted with chloroform, methylene chloride or ethyl acetate, washed with water and dried to give the product.

Compounds of general formulas 1 and 2 wherein $R_4$ is aminoalkanoyloxymethyl are prepared by mixing a suspension of a salt, for example, the alkali metal or the triethylammonium salt of an acid of general formula 1, for example, the sodium salt, and an excess of an appropriate amine protected aminoalkanoyloxymethyl halide in a solvent such ad dimethylformamide, hexamethylphosphoraide or dimethylsulfoxide for 2 to 96 hours at 10° to 30° C. The mixture is then diluted with a solvent such as ethyl acetate or methylene chloride, washed with water, aqueous base, then water. The organic phase is separated and the precipitate isolated by conventional means.

Compounds of formula 3 are prepared by different routes depending upon the isomer required.

The compounds of formula 4 where n is 0, 1 or 2 are prepared by a modification of the procedure of

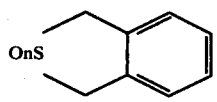

Formula 4

Oliver, et al., in Chem. and Ind., 1024 (1965). α,α-Dibromo-o-xylene is reacted with sodium sulfide in ethanol to form 1,3-dihydrobenzo[c]thiophene. The thiophene compound is oxidized to the corresponding dioxide by means of hydrogen peroxide, m-chloroperzenxoic acid or other suitable oxidants or to the monoxide (Can. J. Chem., 51, 4082 (1973) using sodium metaperoidate.

A compound of formula 3 wherein n is 2 and $R_1$ is benzoyl and with the substitution at position 5 is prepared by a modification of the procedure in Tetrahedron, 31, 863 (1975). Equimolar amounts of the compound of formula 4 wherein n is 2 and α-hydroxy hippuric acid are mixed together in a suitable solvent such as concentrated (50% to 100% $H_2SO_4$) sulfuric acid or 50% to 95% sulfuric acid-50% to 5% glacial acetic acid mixture at 0° C. After stirring for 1-3 hours at 0° C., the reaction mixture is stirred at 10° to 30° C. for from 10 hours to 3 days. The reaction product, α-benzamido(1,3-dihydrobenzo[c]thien-5-yl)acetic acid 2,2-dioxide, is recovered by conventional methods. Substituting 1,3-dihydrobenzo[c]thiophene 2-oxide or 1,3-dihydrobenzo[c]thiophene for the corresponding dioxide gives the corresponding benzamido compounds, namely, α-benzamido(1,3-dihydrobenzo[c]thien-5-yl)acetic acid respectively.

Compounds of formula 3 wherein n is 0, 1 or 2 and $R_1$ is H, and substitution at position 5, said compounds being isolated as an acid salt, are prepared from the corresponding compounds of formula 3 wherein $R_1$ is benzoyl. A compound of formula 3 wherein n is 2 and $R_1$ is benzoyl, substitution at position 5 is heated at reflux for 1-6 hours in a suitable acid such as hydrochloric, hydrobromic, sulfuric or phosphoric acid. Neutralization of the amino acid salt gives the free amino acid.

Compounds of formula 3 wherein n is 0 or 1 and $R_1$ is benzoyl are treated with a suitable acid such as hydrochloric, hydrobromic, sulfuric or phosphoric acid at reflux for 1 to 6 hours to give the acid salts of compounds of formula 3 wherein n is 0 or 1 and $R_1$ is hydrogen, namely, α-amino(1,3-dihydrobenzo[c]thien-5-yl)acetic acid and α-amino(1,3-dihydrobenzo[c]thien-5-yl)acetic acid 2-oxide respectively.

The thus formed acid salts of the amino acid and the amino acids of formula 3 wherein R is hydrogen and n is 0, 1 and 2 and substitution of the dihydrobenzo[c]thiophene ring is at the 5 position are deemed part of this invention as they are intermediates required for the preparation of cephalosporin compounds as represented by formula 1 which are useful as antibacterials.

Neutralization of the amino acid salts described above with a base, for example, sodium hydroxide, sodium bicarbonate, ammonium hydroxide or a basic ion exchange resin Amberlite IR45 ® in water or alcohol at 0° to 40° C. for from 10 minutes to 2 hours gives the amino acid in a zwitter ion form. Other amino acid salts described herein are neutralized in a similar manner. The amino acid in the zwitter ion form can be reacted with an acid to form the corresponding acid addition salt. Acids which may be reacted with the zwitter ion form are hydrochloric, hydrobromic, hydroiodic, sulfuric, phosphoric acetic, maleic, citric, succinic, tartaric, fumaric, malic and ascorbic in water or alcohol at 0° to 40° C. for 10 minutes to 2 hours.

Compounds as represented by formula 3 with substitution at position 5, n is 0, 1 or 2, $R_1$ is alkoxycarbonyl group (1 to 4 carbon alkoxy group) or a 2 to 5 carbon alkanoyl group are prepared from the corresponding compounds of formula 3 wherein $R_1$ is hydrogen by reacting the hydrochloride salt or the free amino acid in a suitable solvent such as ethyl ether, tetrahydrofuran, dioxane, chloroform, benzene or a water-dioxane mixture with an appropriate alkoxycarbonylazide or an alkanoyl halide optionally in the presence of a basic material, for example, triethylamine, sodium bicarbonate or potassium carbonate.

An equivalent amount of an alkoxycarbonylazide, the alkoxy group contains from 1 to 4 carbon atoms, such as ethoxycarbonylazide, propoxycarbonylazide or tert-butoxycarbonylazide, is reacted with the α-amino compound at 0° to 50° C. for from 1 to 24 hours. Or an equivalent amount of a 2 to 5 carbon acid halide, the halide being chlorine or bromine, such as acetyl chloride, propionyl chloride or butyryl bromide is reacted in a suitable solvent in the presence of a basic material with the α-amino compound at 0° to 50° C. for from 1 to 24 hours.

Compounds represented by formula 3 in which $R_1$ is hydrogen and n is 0 with substitution at position 4 may be prepared as follows:

1,3-Dihydrobenzo[c]thiophene 2,2-dioxide, previously described, is brominated with 1 equivalent of bromine in carbon tetrachloride solution in the presence of iron [CA 84, 89930 (1976)] at reflux until the bromine color disappears to give 4-bromo-1,3-dihydrobenzo[c]-thiophene 2,2-dioxide.

The bromo compound described above is dissolved in quinoline and mixed with an equivalent amount of cuprous cyanide. This mixture is heated for 6 to 12 hours at 100° C. to about 160° C. 4-Cyano-1,3-dihydrobenzo[c]thiophene 2,2-dioxide is recovered from the reaction mixture.

Using the method of Brown, et al., *J. Am. Chem. Soc.*, 86, 1085 (1964), 4-cyano-1,3-dihydrobenzo[c]thiophene 2,2-dioxide is reduced using lithium triethoxyaluminohydride. The aluminohydride compounds (5 equivalents) in a solvent, for example, ethyl ether or tetrahydrofuran at about 0° C. to 10° C. is reacted with 4-cyano-1,3-dihydrobenzo[c]thiophene 2,2-dioxide for about 1 to 2 hours, hydrolyzing the complex formed with an acid such as hydrochloric, sulfuric or phosphoric, and recovering 4-formyl-1,3-dihydrobenzo[c]thiophene.

Equimolar amounts of 4-formyl-1,3-dihydrobenzo[c]thiophene dissolved in a low molecular weight alcohol such as ethanol or methanol and sodium cyanide and ammonium chloride, both dissolved in water, are mixed and stirred at 10° C. to 30° C. for 1-4 hours. The reaction product is refluxed for 1 to 2 hours with an acid, for example, hydrochloric acid or sulfuric acid and after neutralization with a base such as sodium hydroxide, α-amino(1,3-dihydrobenzo[c]thien-4-yl)acetic acid is obtained.

Compounds of formula 3 wherein n is 0 and $R_1$ is an alkoxycarbonyl group in which the alkoxy group has from 1 to 4 carbon atoms or a 2 to 5 carbon alkanoyl group and the substitution is at position 4 are prepared from the corresponding compounds wherein $R_1$ is hydrogen. An equivalent amount of an alkoxycarbonylazide, the alkoxy group contains from 1 to 4 carbon atoms such as ethoxycarbonylazide, propoxycarbonylazide or isobutoxycarbonylazide is reacted with the α-amino compound in a suitable solvent optionally in the presence of a basic material at 0° to 50° C. for from 1 to 24 hours; or an equivalent amount of a 2 to 5 carbon acid halide, the halide being chlorine or bromine, such as acetyl chloride, propionyl chloride or butyryl bromide is reacted in a suitable solvent optionally in the presence of a basic material at 0° to 50° C. for from 1 to 24 hours. A suitable solvent may be selected from ethyl ether, tetrahydrofuran, dioxane, chloroform, benzene or water dioxane which optionally may contain a basic material such as triethylamine bicarbonate or potassium carbonate.

Compounds of formula 3 wherein n is 2 and $R_1$ is other than hydrogen and the substitution is at the 4 position are prepared by reacting the corresponding compounds wherein n is 0 in a suitable solvent such as water or chloroform with 2 to 2.5 equivalents of an oxidizing agent such as m-chloroperbenzoic acid, peracetic acid or hydrogen peroxide at 0° to 30° C. for from 2 to 18 hours.

Those compounds of formula 3 wherein n is 1, $R_1$ is other than hydrogen and the substitution is at position 4 are prepared by reacting the corresponding compounds wherein n is 0 in a suitable solvent such as water or chloroform with 1 to 1.1 equivalents of an alkali metal (sodium or potassium) metaperoidate at 0° to 30° C. for from 2 to 18 hours.

Compounds of formula 3 wherein n is 1 or 2 and the substitution is at position 4 and $R_1$ is hydrogen may be prepared by hydrolyzing the corresponding compounds wherein $R_1$ is other than hydrogen in a suitable solvent such as water in the presence of an acid such as hydrochloric, hydrobromic, sulfuric or phosphoric for from 1 to 10 hours at from 30° to 100° C. The resulting acid addition salt thus formed may be reacted with a suitable basic material such as sodium hydroxide, potassium carbonate, sodium bicarbonate, ammonia or Amberlite IR45 ® in water at from 0° to 30° C. for from 10 to 60 minutes to yield the free amino acid.

Compounds of formula 3 wherein $R_1$ and n are as defined for formula 3 and substitution of the dihydrobenzo[c]thiophene ring is at position 4 are deemed part of this invention as these materials are intermediates used in the preparation of cephalosporin compounds of general formula 1 which are useful as antibacterials.

Compounds represented by formula 3 wherein n is 0, 1 or 2 and $R_1$ is hydrogen and the 1,3-dihydrobenzo[c]thiophene ring system is substituted at position 4 are reacted with acids, for example, hydrofluoric, hydrobromic, hydriodic, sulfuric, phosphoric, maleic, trifluoroacetic, citric, succinic, tartaric, fumaric, malic or ascorbic, to form the corresponding acid salts or with bases, such as sodium hydroxide, calcium oxide, magnesium hydroxide, potassium hydroxide, ammonium hydroxide, triethylamine, dibutylamine, octylamine to form the corresponding salts.

Compounds of formula 3 are optically active and are deemed a part of this invention.

Compounds represented by formula 3 wherein n is 0, 1 or 2, $R_1$ is hydrogen and substitution is at position 4 or 5 may be resolved into the D and L isomers using binaphthylphosphoric acid (BPA).

About 2 to 3 equivalents of the racemic mixture (D,L) of the compound of formula 3, n is 0, 1 or 2, $R_1$ is hydrogen and substitution is at position 4 or 5, 1 to 2 equivalents of (+)-BPA and 1 to 3 equivalents of hydrogen chloride in methanol are refluxed for 10 to 60 minutes. The salt formed between (+)-BPA and the (D)-α-amino acid (a compound of formula 3 defined above) is separated and then reacted with sodium acetate trihydrate in methanol for 0.5 to 2 hours at reflux. The appropriate (D)-α-amino acid is recovered.

EXAMPLE 1

3-[(Acetyloxy)methyl]-7-amino-8-oxo-5-thia-1-azabicyclo[4.2.0]oct-2-ene-2-carboxylic acid tert-butyl ester 3-[(Acetyloxy)methyl]-7-amino-8-oxo-5-thia-1-azabicyclo[4.2.0]oct-2-ene-2-carboxylic acid (0.04 mole) is added to 100 ml of dioxane, 10 ml of concentrated sulfuric acid and 50 ml of liquid isobutylene in a pressure bottle. The mixture is shaken overnight. The bottle is chilled, opened and the contents poured into an ice cold solution of sodium bicarbonate. Extraction of the aqueous phase with ethyl acetate followed by drying and evaporation of the ethyl acetate phase gives the title compound, M.P. 111°–112° C. See *J. Med. Chem.*, 9, 444 (1966).

In like manner using sufficient quantities of 7-amino-3-methyl-8-oxo-5-thia-1-azabicyclo[4.2.0]oct-2-ene-2-carboxylic acid and 7-amino-3-[[(5-methyl-1,3,4-thiadiazol-2-yl)thio]methyl]-8-oxo-5-thia-1-azabicyclo[4.2.0]oct-2-ene-2-carboxylic acid in place of 3-[(acetyloxy)methyl]-7-amino-8-oxo-5-thia-1-azabicyclo[4.2.0]oct-2-ene-carboxylic acid gives the corresponding tert-butyl esters:

7-amino-3-methyl-8-oxo-5-thia-1-azabicyclo[4.2.0]oct-2-ene-2-carboxylic acid tert-butyl ester; and 7-amino-3-[[(5-methyl-1,3,4-thiadiazol-2-yl)thio]methyl]-8-oxo-5-thia-1-azabicyclo[4.2.0]oct-2-ene-2-carboxylic acid tert-butyl ester.

EXAMPLE 2

1,3-Dihydrobenzo[c]thiophene 2,2-dioxide

This is a modification of the procedure described in Chem. & Ind., 1024 (1965).

α,α'-Dibromo-o-xylene (105.6 g, 0.40 m) is extracted using a Soxhlet extractor into one liter of ethanol containing 50 g (0.64 m) of sodium sulfide over a period of 16 hours. At the end of this time, the reaction mixture is filtered to remove the unreacted sodium sulfide and the ethanol is evaporated. The residue remaining is steam distilled. The distillate is separated into an aqueous and an organic portion. The organic portion is dissolved in methylene chloride, dried over sodium sulfate and the methylene chloride is removed. Distillation of the residue gives 26.5 g (49%) of 1,3-dihydrobenzo[c]thiophene.

1,3-Dihydrobenzo[c]thiophene (3.5 g, 0.026 m) is dissolved in 100 ml of chloroform and cooled to about 0° C. To this solution is added, over a period of 2.5 hours, 10.5 g (0.061 m) of m-chloroperbenzoic acid dissolved in 120 ml of chloroform. The temperature of the reaction mixture is raised to about 20°–25° C. and the mixture stirred for about 18 hours. The chloroform solution is extracted with aqueous sodium bicarbonate and water and then dried over magnesium sulfate. Removal of some of the chloroform results in the precipitation of 1,3-dihydrobenzo[c]thiophene 2,2-dioxide in about a 75% yield. A M.P. 150°–151° C. is obtained for the solid product.

EXAMPLE 3

α-Benzamido(1,3-dihydrobenzo[c]thien-5-yl)acetic acid 2,2-dioxide

Concentrated sulfuric acid (300 ml, 96%) is cooled to about 0° C. Then 26.2 g (0.156 m) of 1,3-dihydrobenzo[c]thiophene 2,2-dioxide and 27 g (0.14 m) of 2-hydroxy-2-benzamido acetic acid (Tetrahedron, 31,863 (1975)) is added and the mixture stirred for one hour. The reaction mixture is warmed to room temperature and stirring is continued for 24 hours. The sulfuric acid solution is poured into ice and water at 0° C. and the aqueous mixture is extracted with ethyl acetate. The ethyl acetate extracts are then extracted with aqueous sodium bicarbonate. The pH of the bicarbonate extract is adjusted to about 2.5 with 1 N hydrochloric acid and extracted with ethyl acetate. The phases are separated and the aqueous phase is extracted a second time with ethyl acetate. The ethyl acetate extracts are combined, dried and concentrated until crystallization began. The title compound is filtered and dried, M.P. 234°–235° C. (dec.).

| Microanalysis | C | H | N | S |
|---|---|---|---|---|
| Calc. | 59.1 | 4.38 | 4.06 | 9.28 |
| Found | 59.05 | 4.71 | 3.66 | 9.03 |

EXAMPLE 4

α-Amino(1,3-dihydrobenzo[c]thien-5-yl)acetic acid 2,2-dioxide, hydrochloride

α-Benzamido(1,3-dihydrobenzo[c]thien-5-yl)-5-acetic acid 2,2-dioxide, hydrochloride (17.25 g, 50 mM) is suspended in 500 ml of 6 N hydrochloric acid and the mixture is refluxed for 5 hours. The solution is cooled to room temperature and filtered to remove benzoic acid. Then the filtrate is concentrated to 100 ml, cooled to precipitate the product and filtered. About 10.7 g (about 75%) of α-amino(1,3-dihydrobenzo[c]thien-5-yl)-5-acetic acid 2,2-dioxide, hydrochloride, hemihydrate; M.P. 194°–196° C. is obtained.

| Microanalysis | C | H | N | S | $H_2O$ |
|---|---|---|---|---|---|
| Calc. | 41.88 | 4.57 | 4.88 | 11.18 | 3.14 |
| Found | 41.86 | 4.52 | 4.89 | 11.16 | 3.4 |

EXAMPLE 5 tert-Butoxycarbonylamino(1,3-dihydrobenzo[c]thien-5-yl)-acetic acid 2,2-dioxide

α-Amino(1,3-dihydrobenzo[c]thien-5-yl)acetic acid 2,2-dioxide, hydrochloride (2.7 g, 10 mM) is dissolved in a mixture of 100 ml of dioxane and 100 ml of water. Triethylamine (6 ml) and tert-butoxycarbonylazide (1.5 ml) are added to the water-dioxane solution. This solution is stirred for 18 hours at room temperature. Dioxane is evaporated and is replaced by ethyl acetate. The pH of the aqueous phase is adjusted to 2.5 by the addition of 1 N hydrochloric acid. After thorough mixing, the ethyl acetate is separated from the aqueous phase. The aqueous phase is extracted a second time with ethyl acetate. The ethyl acetate extracts are combined and dried over magnesium sulfate. Evaporation of the ethyl acetate gives 3.2 g (94%) of tert-butoxycarbonylamino(1,3-dihydrobenzo[c]thien-5-yl)acetic acid 2,2-dioxide in the form of a white foam. The solid crystallizes with 1 mole of dioxane, NMR  Solvent DMSO-$d_6$
TMS internal standard
δ 1.25 (strong, 9H)
δ 4.32 (strong, 4H)
δ 4.97 (d, j=4, 1H)
δ 7.1–7.9 (medium, 5H)

In like manner using this general procedure substitution of α-amino(1,3-dihydrobenzo[c]thien-5-yl)acetic acid and (D)-α-amino(1,3-dihydrobenzo[c]thien-5-yl)acetic acid 2-oxide for (D)-α-amino(1,3-dihydrobenzo[c]thien-5-yl)-acetic acid 2,2-dioxide gives the respective compounds:

(D)-α-(tert-butoxycarbonyl)amino(1,3-dihydrobenzo[c]thien-5-yl)acetic acid; and
(D)-α-(tert-butoxycarbonyl)amino(1,3-dihydrobenzo[c]thien-5-yl)acetic acid 2-oxide.

EXAMPLE 6

α-Amino(1,3-dihydrobenzo[c]thien-5-yl)acetic acid 2-oxide, hydrochloride

To a rapidly stirred solution of sodium metaperiodate (0.12 m) in water (230 ml) is added dropwise molten 1,3-dihydrobenzo[c]thiophene (0.11 m). The mixture is stirred at room temperature for 1 hour and then cooled to 0° for 3 hours. The white precipitate (sodium iodate) is removed by filtration and washed with cold water. The filtrate and washings are extracted with methylene chloride. The methylene chloride is evaporated to give crude yellow crystals. The solid is dissolved in ether, filtered through alumina to remove the colored impurities and the ether is evaporated. The solid is recrystallized from benzene-pentane, M.P. 89°–91° C.

1,3-Dihydrobenzo[c]thiophene 2-oxide is reacted with α-hydroxy hippuric acid according to the procedure described in Example 3 to give α-benzamido(1,3-dihydrobenzo[c]thien-5-yl)acetic acid 2-oxide, which is then hydrolyzed with hydrochloric acid using the general procedure described in Example 4 to give the title compound.

EXAMPLE 7

α-Amino(1,3-dihydrobenzo[c]thien-5-yl)acetic acid, hydrochloride 1,3-Dihydrobenzo[c]thiophene is reacted with α-hydroxy hippuric acid according to the procedure described in Example 3. The resulting compound, α-benzamido(1,3-dihydrobenzo[c]thien-5-yl)acetic acid is then hydrolyzed to the amine using the procedure of Example 4. The title compound is isolated from the reaction mixture.

EXAMPLE 8

4-Cyano-1,3-dihydrobenzo[c]thiophene 2,2-dioxide 1,3-Dihydrobenzo[c]thiophene 2,2-dioxide [Chem. & Ind., 1024 (1965)] is brominated according to the method described in Khim. Tadzh., 107 (1973), [C.A., 84, 89,930 (1976)], using bromine (1.1 equivalents) in refluxing carbon tetrachloride which contains iron until the bromine color is dissipated. Removal of the carbon tetrachloride and recrystallization from ethanol gives 4-bromo-1,3-dihydrobenzo[c]thiophene 2,2-dioxide.

4-Bromo-1,3-dihydrobenzo[c]thiophene 2,2-dioxide (0.1 m) is dissolved in dry quinoline. To the quinoline solution is added (0.1 M) of cuprous cyanide. The temperature of the mixture is maintained between 100°–160° C. for about 6 to 12 hours. At the end of this time the mixture is poured into water and concentrated ammonium hydroxide. Benzene is added and the mixture is stirred until the solids are dissolved. Ethyl ether is added and the mixture is filtered to remove undissolved solids. The organic and aqueous phases are separated and the aqueous phase is discarded. The organic phase is then washed with 6 N ammonium hydroxide, 6 N hydrochloric acid and saturated sodium chloride. Removal of the benzene-ethyl ether gives the title compound which is used without further purification.

EXAMPLE 9

4-Formyl-1,3-dihydrobenzo[c]thiophene

Lithium triethoxyaluminohydride (5 equivalents) is prepared in 150 ml of ethyl ether according to the method described in J. Am. Chem. Soc., 86, 1085 (1964). This solution, at a temperature of about 0° C., is added over a period of about 15 minutes to an ethyl ether solution of 4-cyano-1,3-dihydrobenzo[c]thiophene 2,2-dioxide (1 equivalent) maintained at about 0° C. The temperature of the mixture rises to about 10° C. The mixture is stirred for an additional 60 minutes to about 0° C. Addition of 6 N hydrochloric acid decomposes the complex present in the mixture. The organic and aqueous phases are separated and the aqueous phase is extracted with ethyl ether. The ether fractions are combined and are extracted with aqueous sodium bicarbonate and water. Drying over magnesium sulfate precedes the evaporation of ether to give 4-formyl-1,3-dihydrobenzo[c]thiophene.

EXAMPLE 10

α-Amino(1,3-dihydrobenzo[c]thien-4-yl)acetic acid

About 16.5 g (0.1 m) of 4-formyl-1,3-dihydrobenzo[c]thiophene is dissolved in methanol. The methanol solution is added to a solution of (0.1 m) of sodium cyanide and (0.1 m) of ammonium chloride dissolved in water. The mixture is stirred two hours at room temperature, diluted with water and extracted with benzene. The benzene extracts are washed with water and then extracted with 6 N hydrochloric acid. The hydrochloric acid extract is heated to reflux for two hours, filtered and partially neutralized with ammonium hydroxide to precipitate the amino acid. The title compound is filtered, washed with ethyl ether and hot 95% ethanol prior to drying in vacuum.

EXAMPLE 11

α-(tert-butoxycarbonyl)amino(1,3-dihydrobenzo[c]thien-4-yl)acetic acid

α-Amino(1,3-dihydrobenzo[c]thien-4-yl)acetic acid hydrochloride (0.01 m) is dissolved in a mixture of equal parts of water and dioxane. Triethylamine (0.01 m) and tert-butoxycarbonylazide (0.01 m) are added to the mixture which is stirred for 18 hours at room temperature. The dioxane is evaporated from the mixture, ethyl acetate is added and the pH of the aqueous phase is adjusted to about 2.5 with the addition of 1 N hydrochloric acid. The phases are separated and the aqueous phase is extracted a second time with additional ethyl acetate. The ethyl acetate is separated from the aqueous phase. These extracts are combined and dried over magnesium sulfate. Evaporation of the ethyl acetate gives α-(tert-butoxycarbonyl)amino(1,3-dihydrobenzo[c]thien-4-yl)acetic acid.

EXAMPLE 12

α-Amino(1,3-dihydrobenzo[c]thien-4-yl)acetic acid, 2,2-dioxide

α-(tert-Butoxycarbonyl)amino(1,3-dihydrobenzo[c]thien-4-yl)acetic acid (0.05 m) is added to chloroform and the mixture cooled to about 0° C. Over a period of about 2.5 hours, 0.12 moles of m-chloroperbenzoic acid dissolved in chloroform is added to the mixture maintained at 0° C. When the addition of the m-chloroperbenzoic acid is complete, the temperature of the mixture is raised to about 20° to 25° C. from about 0° C. and stirred for about 18 hours, chilled to 0° C. to precipitate the m-chlorobenzoic acid which is filtered from the solution. Removal of a portion of the chloroform results in the precipitation of Amino(1,3-dihydrobenzo[c]thien-4-yl)acetic acid, 2-oxide This oxidation method is adopted from the method described in Can. J. Chem., 51, 4082 (1973).

To a solution of sodium metaperiodate (0.12 mole) in water, vigorously stirred, is added 0.11 mole of α-(tert-butoxycarbonyl)amino(1,3-dihydrobenzo[c]thien-4-yl)acetic acid. This mixture is stirred at room temperature for about 1 hour and then cooled to 0° C. for three hours. The precipitate, sodium iodate, is removed by filtration after which the filtrate is extracted with methylene chloride. The extracts are dried and the methylene chloride is evaporated. The crude residue is recrystallized from ethyl acetate to give α-(tert-butoxycarbonyl)amino(1,3-dihydrobenzo[c]thien-4-yl)acetic acid 2-oxide which is hydrolyzed according to the procedure described in Example 4 to give the title compound.

EXAMPLE 14

7-[[amino(1,3-dihydrobenzo[c]thien-5-yl)acetyl]amino]-3-methyl-8-oxo-5-thia-1-azabicyclo[4.2.0]oct-2-ene-2-carboxylic acid $S^2$, $S^2$-dioxide tert-Butoxycarbonylamino(1,3-dihydrobenzo[c]thien-5-yl)acetic acid 2,2-dioxide, 5 mM, the tert-butyl ester of 7-amino-3-methyl-8-oxo-5-thia-1-azabicyclo[4.2.0]oct-2-ene-2-carboxylic acid (5 mM) and N-ethoxycarbonyl-2-ethoxy-1,2-dihydroquinoline (5 mM) are dissolved in 100 ml of ethyl acetate. The mixture is stirred for 3-4 hours at room temperature (about 15°-20° C.). The ethyl acetate solution is then extracted with 100 ml of aqueous sodium bicarbonate, 100 ml of 1 N hydrochloric acid and 50 ml of saturated sodium chloride solution. The ethyl acetate solution is dried over anhydrous magnesium sulfate and filtered. Evaporation of the ethyl acetate gives 2.7 g (about 90%) of the coupled product, namely, the tert-butyl ester of 7-[[(tert-butoxycarbonyl)amino(1,3-dihydrobenzo[c]thien-5-yl)acetyl]amino]-3-methyl-8-oxo-5-thia-1-azabicyclo[4.2.0]oct-2-ene-2-carboxylic acid $S^2,S^2$-dioxide.

Without further purification 2.3 g of the coupled product in 100 ml of trifluoroacetic acid (TFA) is maintained under a nitrogen atmosphere and is stirred at 0° C. about 30 minutes. The solution is warmed to room temperature (15°-20° C.) and stirred an additional 30 minutes. The TFA is evaporated using a rotary evaporator while maintaining the temperature of the solution at 25° C. The residue remaining from the evaporation of the TFA is solidified by the addition of ethyl ether. The solid is filtered and dried in a vacuum overnight. The yield is 2.2 g (about 100%) of the TFA salt of 7-[[amino(1,3-dihydrobenzo[c]thien-5-yl)acetyl]amino]-3-methyl-8-oxo-5-thia-1-azabicyclo[4.2.0]oct-2-ene-2-carboxylic acid $S^2,S^2$-dioxide which is dissolved in 75 ml of water and 75 ml of methanol. The pH of the solution is adjusted to 4.5 by the addition of Amberlite IR45 ® resin. The resin is removed from the solution by filtration and the water methanol is evaporated. The residue is triturated with ethanol and the solid filtered and dried in a vacuum. The yield of 7-[[amino(1,3-dihydrobenzo[c]thien-5-yl)acetyl]amino]-3-methyl-8-oxo-5-thia-1-azabicyclo[4.2.0]oct-2-ene-2-carboxylic acid $S^2,S^2$-dioxide is 0.9 g (about 40%). M.P. is 235°-238° C. (dec).

| Microanalysis | C | H | N | S |
|---|---|---|---|---|
| Calc. | 49.41 | 4.38 | 9.60 | 14.66 |
| Found | 48.79 | 4.61 | 9.29 | 14.69 |

EXAMPLE 15

3-[[(Acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide α-(tert-Butoxycarbonyl)amino(1,3-dihydrobenzo[c]thien-5-yl)acetic acid 2,2-dioxide (5 mM) is dissolved in 50 ml of tetrahydrofuran (THF) to which 5 mM of triethylamine is added. The THF solution is cooled to 0° C. and 5 mM of iso-butyl chloroformate is added. This mixture is stirred for 30 minutes to insure formation of the mixed anhydride. A solution of 3-[(acetyloxy)methyl]-7-amino-8-oxo-5-thia-1-azabicyclo[4.2.0]oct-2-ene-2-carboxylic acid (5 mM) and triethylamine (6 mM) in a mixture of 25 ml of the THF and 25 ml of water is added to the solution containing the mixed anhydride. The resulting mixture is stirred for 1 hour at 0° C. and then warmed to room temperature (15°-20° C.). The reaction mixture is poured into 100 ml of water and extracted with 2×120 ml ethyl acetate. The pH of the aqueous phase is adjusted to about 2.5 with 1 N hydrochloric acid. Ethyl acetate is used to twice extract the aqueous phase. These extracts are combined and dried over magnesium sulfate. After removal of the magnesium sulfate, the ethyl acetate is removed to give 2.3 g (about 80%) of the coupled acid, namely, 3-[(acetyloxy)methyl]-7-[[(tert-butoxycarbonyl)amino(1,3-dihydrobenzo[c]thien-5-yl)acetyl]amino]-8-oxo-5-thia-1-azabicyclo[4.2.0]oct-2-ene-2-carboxlyic acid $S^2,S^2$-dioxide. Thin layer chromatography indicates that only one compound is present. Without further purification, the coupled acid (2.2 g, 3.7 mM) is dissolved in 50 ml of cold (0° C.) TFA. The solution is stirred at 0° C. for about one hour, warmed to room temperature and stirred an additional one-half hour. The TFA is evaporated on a rotary vacuum evaporator while maintaining the solution temperature at 25° C. The resulting residue is solidified by the addition of ethyl ether. The solid is separated and dried under vacuum. The crude TFA salt of the coupled acid is dissolved in 100 ml of methanol and 6 N ammonium hydroxide is added until the pH was 4.5. The solution is evaporated to near dryness, ethanol is added and then part of the ethanol is removed by distillation so as to remove any water by azeotropic distillation. Ether addition to the ethanol solution causes the precipitation of 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide as a white solid. The solid is filtered and dried under vacuum, M.P. 260° C. Total yield is 1.3 g (about 70%). A purity of 85% is indicated by high pressure liquid chromotography.

In a manner similar to that described above, 7-amino-3-[[(5-methyl-1,3,4-thiadiazol-2-yl)thio]methyl]-8-oxo-5-thia-1-azabicyclo[4.2.0]oct-2-ene-2-carboxylic acid is substituted for 3-[(acetyloxy)methyl]-7-amino-8-oxo-5-thia-1-azabicyclo[4.2.0]oct-2-ene-2-carboxylic acid to produce 7-[[amino(1,3-dihydrobenzo[c]thien-5-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid $S^2,S^2$-dioxide, M.P 175°-180° C.

EXAMPLE 16

3-[(Acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide Using the method of Flynn, U.S. Pat. No. 3,252,973, α-(tert-butoxycarbonyl)amino(1,3-dihydrobenzo[c]thien-5-yl)acetic acid 2,2-dioxide, 3 equivalents, is dissolved in water, the pH of which is adjusted to 6.6 by the addition of sodium hydroxide. 3-[(Acetyloxy)methyl]-7-amino-8-oxo-5-thia-1-azabicyclo[4.2.0]oct-2-ene-2-carboxylic acid $S^2,S^2$-dioxide, 1 equivalent, is added. Then 1 equivalent dicyclohexylcarbodiimide in dioxane is added to the mixture. After about 18 hours at about 5° C., the reaction mixture is filtered and the filtrate is then evaporated. The tert-butoxycarbonyl group is removed from the coupled compound according to the general procedure described in U.S. Pat. No. 3,657,232 to give the title compound.

EXAMPLE 17

7-[[(D)-α-Amino(1,3-dihydrobenzo[c]thien-5-yl)acetyl-]amino-3-methyl-8-oxo-5-thia-1-azabicyclo[4.2.0]oct-2-ene-2-carboxylic acid, $S^2,S^2$-dioxide (D)-α-(tert-Butoxycarbonyl)amino(1,3-dihydrobenzo[c]thien-5-yl)acetic acid 2,2-dioxide (0.01 m) is reacted with a slight molar excess of thionyl chloride to form the corresponding acid chloride. A chloroform solution of (D)-α-(tert-butoxycarbonyl)amino(1,3-dihydrobenzo[c]thien-5-yl)acetyl chloride 2,2-dioxide (0.05 m) is mixed with a chloroform solution of 7-amino-3-methyl-8-oxo-5-thia-1-azabicyclo[4.2.0]oct-2-ene-2-carboxylic acid (0.05 m) and an acid acceptor (0.05 m) such as triethylamine at room temperature. After stirring for 1–3 hours the mixture is filtered and the chloroform evaporated. The residue is taken up in ethyl acetate. The ethyl acetate solution is dried and evaporated. Removal of the tert-butoxycarbonyl group according to the general procedure in U.S. Pat. No. 3,657,232, followed by neutralization of the acid salt gives the title compound. The residue is treated according to the general procedure in U.S. Pat. No. 3,657,232 to remove the tert-butoxycarbonyl group and then treated to neutralize the TFA so as to produce the title compound.

Using procedures described in Examples 14, 15, 16 and 17, the cephalosporin derivatives listed below can be prepared from the appropriate starting materials.

| 7-AMINO CEPHALOSPORIN | AMINO ACID | SUBSTITUED 7 AMINO CEPHALOSPORIN |
|---|---|---|
| 3-[(acetyloxy)methyl]-7-amino-8-oxo-5-thia-1-azabicyclo-8 4.2.0]oct-2-ene-2: carboxylic acid | α-(tert-butoxycarbonyl)amino-(1,3-dihydrobenzo[c]thien-5-yl)acetic acid 2,2-dioxide | 3-[(acetyloxy)methyl]-7-[[amino(1,3-dihydrobenzo-[c]thien-5-yl)acetyl]amino]-8-oxo-5-thia-1-azabicyclo-[4.2.0]oct-2-ene-2-carboxylic acid $S^2$, $S^2$-dioxide |
| 7-amino-3[[(5-methy 1-1,3,4-thiadiazol-2-yl)thio]methyl]-8-oxo-5-thia-1-azabicyclo-[4.2.0]oct-2-ene-2-carboxylic acid | α-(tert-butoxycarbonyl)amino-(1,3-dihydrobenzo [c]thien-5-yl)acetic acid 2,2-dioxide | 7-[[amino(1,3-dihydrobenzo-[c]thien-5-yl)acetyl]amino]-3-[[(5-methyl-1,3,4-thiadiazol-2-yl)thio]methyl]-8-oxo-5-thia-1-azabicyclo[4.2.0]-oct-2-ene-2-carboxylic acid $S^2$-dioxide |
| 7-amino-3-[[1,3,4-thiadiazol-2-yl]thio]methyl]-8-oxo-5-thia-1-azabicyclo[4.2.0]oct-2-ene-2-carboxylic acid | α-(tert-butoxycarbonyl)amino-(1,3-dihydrobenzo[c]thien-5-yl)acetic acid 2,2-dioxide | 7-[[amino(1,3-dihydrobenzo-[c]thien-5-yl) acetyl]amino]-3-[[1,3,4-thiadiazol-2-yl]-thio]methyl]-8-oxo-5-thia-1-azabicyclo[4.2.0]oct-2-ene-2-carboxylic acid $S^2$, dioxide |
| 7-amino-3-[[(tetrazol-5-yl)-thio]methyl]-8-oxo-5-thia-1-azabicyclo[4.2.0]oct-2-ene-2- | α-(tert-butoxycarbonyl)amino-(1,3-dihydrobenzo[c]thien-5-yl)acetic acid 2,2-dioxide | 7-[[amino(1,3-dihydrobenzo-[c]thien-5-yl)acetyl]amino]-3-[[tetrazol-5-yl)thio]-methyl]-8-oxo-5-thia-1-azabicyclo[4.2.0]oct-2-ene-2-carboxylic acid $S^2$, $S^2$-dioxide |
| 7-amino-3-[[1-methyltetrazol-5-yl)thio]methyl]-8-oxo-5-thia-1-azabicyclo[4.2.0]-oct-2-ene-2-carboxylic acid | α-(tert-butoxycarbonyl)amino-(1,3-dihydrobenzo[c]thien-5-yl)acetic acid 2,2-dioxide | 7-[[amino)1,3-dihydrobenzo-[c]thien-5-yl)acetyl]amino]-3-[[1-methyltetrazol-5-yl)-thio]methyl]-8-oxo-5-thia-1-azabicyclo[4.2.0]oct-2-ene-2-carboxylic acid $S^2$, $S^2$-dioxide |
| 7-amino-3-[[(1,3,4-oxadiazol-2-yl)thio]methyl]-8-oxo-5-thia-1-azabicyclo[4.2.0]oct-2-ene-2-carboxylic acid | α-(tert-butoxycarbonyl)amino-(1,3-dihydrobenzo[c]thien-5-yl)acetic acid 2,2-dioxide | 7-[[amino)1,3-dihydrobenzo-[c]thein-5-yl)acetyl]amino]-3-[[(1,3,4-oxadiazol-2-yl)-thio]methyl]-8-oxo-5-thia-1-azabicyclo[4.2.0]oct-2-ene-2-carboxylic acid $S^2$, $S^2$-dioxide |
| 7-amino-3-[[(5-methyl-1,3,4-oxadiazol-2-yl)thio]methyl]-8-oxo-5-thia-1-azabicyclo-[4.2.0]oct-2-ene-2-carboxylic acid | α-(tert-butoxycarbonyl)amino-(1,3-dihydrobenzo[c]thien-5-yl)acetic acid 2,2-dioxide | 7[[amino(1,3-dihydrobenzo-[c]thien-5-yl)acetyl]amino-3-[[(5-methyl-1,3,4-oxadiazol-2-yl)thio]methyl]-8-oxo-5-thia-1-azabiccyclo[4.2.0]-oct-2-ene-2-carboxylic acid $S^2$, $S^2$-dioxide |
| 7-amino-3-[[(1,3,4-triazol-2-yl)thio]methyl]-8-oxo-5-thia-1-azabicyclo[4.2.0]oct-2-ene-2-carboxylic acid | α- (tert-butoxycarbonyl)amino-(1,3-dihydrobenzo[c]thien-5-yl)acetic acid 2,2-dioxide | 7-[[amino(1,3-dihydrobenzo-[c]thien-5-yl)acetyl]amino]-3-[[(1,3,4-triazol-2-yl)-thio]methyl]-8-oxo-5-thia-1-azabicyclo[4.2.0]oct-2-ene-2-carboxylic acid $S^2$, $S^2$ dioxide |
| 7-amino-3-[[(5-methyl-1,3,4-triazol-2-yl)thio]methyl]-8-oxo-5-thia-1-azabicyclo-[4.2.0]oct-2-ene-2-carboxylic acid | α-(tert-butoxycarbonyl)amino-(1,3-dihydrobenzo[c]thien-5-yl)acetic acid 2,2-dioxide | 7-[[amino(1,3-dihydrobenzo-[c]thien-5-yl)acetyl]amino]-3-[[(5-methyl-1,3,4-triazol-2-yl)thio)methyl]-8-oxo-5-thia-1-azabicyclo[4.2.0]oct-2-ene-2-carboxylic acid $S^2$, $S^2$-dioxide |

-continued

| 7-AMINO CEPHALOSPORIN | AMINO ACID | SUBSTITUTED 7 AMINO CEPHALOSPORIN |
|---|---|---|
| 7-amino-3-[[(1,2,3-triazol-5-yl)thio]methyl]-8-oxo-5-thia-1-azabicyclo[4.2.0]-oct-2-ene-2-carboxylic acid | α-(tert-butoxycarbonyl)amino-(1,3-dihydrobenzo[c]thien-5-yl)acetic acid 2,2-dioxide | 7-[[amino(1,3-dihydrobenzo-[c]thien-5-yl)acetyl]amino]-3-[[(1,2,3-triazol-5-yl)-thio]methyl]-8-oxo-5-thia-1-azabicyclo[4.2.0]oct-2-ene-2-carboxylic acid $S^2$, $S^2$-dioxide |
| 7-amino-3-methyl-8-oxo-5-thia-1-azabicyclo[4.2.0]-oct-2-ene-2-carboxylic acid | (D)-α-(tert-butoxycarbonyl)-amino(1,3-dihydrobenzo[c]-thien-4-yl)acetic acid 2,2-dioxide | 7-[[(D)-α-amino(1,3-dihydro-benzo[c]thien-4-yl)acetyl]-amino]-3-methyl-8-oxo-5-thia-1-azabicyclo[4.2.0]oct-2-ene-2-carboxylic acid $S^2$, $S^2$-dioxide |
| 3-[(acetyloxy)methyl]-7-amino-8-oxo-5-thia-1-azabicyclo[4.2.0]oct-2-ene-2-carboxylic acid | (D)-α-(tert-butoxycarbonyl)-amino(1,3-dihydrobenzo[c]-thien-4-yl)acetic acid | 3-[(acetyloxy)methyl]-7-[[(D)-α-amino(1,3-dihydro-benzo[c]thien-4-yl)acetyl]-amino]-8-oxo-5-thia-1-aza-bicyclo[4.2.0]oct-2-ene-2-carboxylic acid |
| 7-amino-3-[[(5-methyl-1,3,4-thiadiazol-2-yl)thio]methyl]-8-oxo-5-thia-1-azabicyclo-[4.2.0]oct-2-ene-carboxylic acid | α-(tert-butoxycarbonyl)amino-(1,3-dihydrobenzo[c]thien-4-yl)acetic acid 2,2-dioxide | 7-[[amino(1,3-dihydrobenzo-[c]thien-4-yl)acetyl]amino]-3-[[(5-methyl-1,3,4-thiadia-zol-2-yl)thio]methyl]-8-oxo-5-thia-1-azabicyclo[4.2.0]-oct-2-ene-2-carboxylic acid $S^2,S^2$-dioxide |
| 7-amino-3-[[(1,3,4-thiadia-zol-2-yl)thio]methyl]-8-oxo-5-thia-1-azabicyclo[4.2.0]-oct-2-ene-2-carboxylic acid | α-(tert-butoxycarbonyl)amino-(1,3-dihydrobenzo[c]thien-4-yl)acetic acid 2,2-dioxide | 7-[[amino(1,3-dihydrobenzo-[c]thien-4-yl)acetyl]amino]-3-[[(1,3,4-thiadiazol-2-yl)-thio]methyl]-8-oxo-5-thia-1-azabicyclo[4.2.0]oct-2-ene-2-carboxylic acid $S^2,S^2$-dioxide |
| 7-amino-3-[[(tetrazol-5-yl)-thio]methyl]-8-oxo-5-thia-1-azabicyclo[4.2.0]oct-2-ene-2-carboxylic acid | (D)-α-(tert-butoxycarbonyl)-amino(1,3-dihydrobenzo[c]-thien-4-yl)acetic acid 2-oxide | 7-[[(D)-α-amino(1,3-dihydro-benzo[c]thien-4-yl)acetyl]-amino]-3-[[(tetrazol-5-yl)-thio]methyl]-8-oxo-5-thia-1-azabicyclo[4.2.0]oct-2-ene-2-carboxylic acid $S^2$-oxide |
| 7-amino-3-[[(1,3,4-oxadia-zol-2-yl)thio]methyl]-8-oxo-5-thia-1-azabicyclo-[4.2.0]oct-2-ene-2-carboxy-lic acid | α-(tert-butyoxycarbonyl)amino-(1,3-dihydrobenzo[c]thien-4-yl)acetic acid 2,2-dioxide | 7-[[amino(1,3-dihydrobenzo-[c]thien-4-yl)acetyl]amino]-3-[[(1,3,4-oxadiazol-2-yl)-thio]methyl]-8-oxo-5-thia-1-azabicyclo[4.2.0]oct-2-ene-2-carboxylic acid $S^2,S^2$-dioxide |
| 7-amino-3-[[(5-methyl-1,3,4-oxadiazol-2-yl)thio]methyl]-8-oxo-5-thia-1-azabicyclo-[4.2.0]oct-2-ene-2-carboxylic acid | α-(tert-butoxycarbonyl)amino-(1,3-dihydrobenzo[c]thien-4-yl)acetic acid 2,2-dioxide | 7-[[amino(1,3-dihydrobenzo-[c]thien-4-yl)acetyl]amino]-3-[[(5-methyl-1,3,4-oxadia-zol-2-yl)thio]methyl]-8-oxo-5-thia-1-azabicyclo[4.2.0]-oct-2-ene-2-carboxylic acid $S^2,S^2$-dioxide |
| 7-amino-3-[[(1,3,4-triazol-2-yl)thio]methyl]-8-oxo-5-thia-1-azabicyclo[4.2.0]-oct-2-ene-2-carboxylic acid | α-(tert-butoxycarbonyl)amino-(1,3-dihydrobenzo[c]thien-4-yl)acetic acid 2,2-dioxide | 7-[[amino(1,3-dihydrobenzo-[c]thien-4-yl)acetyl]amino]-3-[[(1,3,4-triazol-2-yl)-thio]methyl]-8-oxo-5-thia-1-azabicyclo[4.2.0]oct-2-ene-2-carboxylic acid $S^2,S^2$-dioxide |
| 7-amino-3-[[(5-methyl-1,3,4-triazol-2-yl)thio]methyl]-8-oxo-5-thia-1-azabicyclo-[4.2.0]oct-2-ene-2-carboxy-lic acid | α-(tert-butoxycarbonyl)amino-(1,3-dihydrobenzo[c]thien-4-yl)acetic acid 2,2-dioxide | 7-[[amino(1,3-dihydrobenzo-[c]thien-4-yl)acetyl]amino]-3-[[(5-methyl-1,3,4-triazol-2-yl)thio]methyl]-8-oxo-5-thia-1-azabicyclo[4.2.0]-oct-2-ene-2-carboxylic acid $S^2,S^2$-dioxide |
| 7-amino-3-[[(1,2,3-triazol-5-yl)thio]methyl]-8-oxo-5-thia-1-azabicyclo[4.2.0]-oct-2-ene-2-carboxylic acid | α-(tert-butoxycarbonyl)amino-(1,3-dihydrobenzo[c]thien-4-yl)acetic acid 2,2-dioxide | 7-[[amino(1,3-dihydrobenzo-[c]thien-4-yl)acetyl]amino]-3-[[(1,2,3-triazol-5-yl)-thio]methyl]-8-oxo-5-thia-1-azabicyclo[4.2.0]oct-2-ene-2-carboxylic acid $S^2,S^2$-dioxide |
| 7-amino-7-methoxy-3-methyl-8-oxo-5-thia-1-azabicyclo-[4.2.0]oct-2-ene-2-carboxy-lic acid $S^2,S^2$-dioxide | α-(tert-butoxycarbonyl)amino-(1,3-dihydrobenzo[c]thien-4-yl)acetic acid 2,2-dioxide | 7-[[amino(1,3-dihydrobenzo-[c]thien-4-yl)acetyl]amino]-7-methoxy-3-methyl-8-oxo-5-thia-1-azabicyclo[4.2.0]-oct-2-ene-2-carboxylic acid $S^2,S^2$-dioxide |

| 7-AMINO CEPHALOSPORIN | AMINO ACID | SUBSTITUTED 7 AMINO CEPHALOSPORIN |
|---|---|---|
| 3-[(acetyloxy)methyl]-7-amino-7-methoxy-8-oxo-5-thia-1-azabicyclo[4.2.0]-oct-2-ene-2-carboxylic acid $S^2,S^2$-dioxide | α-(tert-butoxycarbonyl)amino-(1,3-dihydrobenzo[c]thien-4-yl)acetic acid 2,2-dioxide | 3-[(acetyloxy)methyl]-7-[[amino(1,3-dihydrobenzo[c]thien-4-yl)acetyl]amino]-7-methoxy-8-oxo-5-thia-1-azabicyclo[4.2.0]oct-2-ene-2-carboxylic acid $S^2,S^2$-dioxide |
| 7-amino-7-methoxy-3-methyl-8-oxo-5-thia-1-azabicyclo-[4.2.0]oct-2-ene-2-carboxylic acid $S^2,S^2$-dioxide | α-(tert-butoxycarbonyl)amino-(1,3-dihydrobenzo[c]thien-5-yl)acetic acid 2,2-dioxide | 7-[[amino(1,3-dihydrobenzo-[c]thien-5-yl)acetyl]amino]-7-methoxy-3-methyl-8-oxo-5-thia-1-azabicyclo[4.2.0]-oct-2-ene-2-carboxylic acid $S^2,S^2$-dioxide |
| 3-[(acetyloxy)methyl]-7-amino-7-methoxy-8-oxo-5-thia-1-azabicyclo[4.2.0]-oct-2-ene-2-carboxylic acid $S^2,S^2$-dioxide | α-(tert-butoxycarbonyl)amino-(1,3-dihydrobenzo[c]thien-5-yl)acetic acid 2,2-dioxide | 3-[(acetyloxy)methyl]-7-[[amino(1,3-dihydrobenzo[c]thien-5-yl)acetyl]amino]-7-methoxy-8-oxo-5-thia-1-azabicyclo[4.2.0]oct-2-ene-2-carboxylic acid $S^2,S^2$-dioxide |
| 3-[(acetyloxy)methyl]-7-amino-8-oxo-5-thia-1-azabicyclo[4.2.0]oct-2-ene-2-carboxylic acid | α-(tert-butoxycarbonyl)amino-(1,3-dihydrobenzo[c]thien-5-yl)acetic acid | 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid |
| 3-[(acetyloxy)methyl]-7-amino-8-oxo-5-thia-1-azabicyclo[4.2.0]oct-2-ene-2-carboxylic acid, tert-butyl ester | α-(tert-butoxycarbonyl)amino-(1,3-dihydrobenzo[c]thien-5-yl)acetic acid 2-oxide | 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2$-oxide |
| 7-amino-3-[[(5-methyl-1,3,4-thiadiazol-2-yl)thio]methyl]-8-oxo-5-thia-1-azabicyclo-[4.2.0]oct-2-ene-2-carboxylic acid | α-(tert-butoxycarbonyl)amino-(1,3-dihydrobenzo[c]thien-5-yl)acetic acid 2-oxide | 7-[[amino(1,3-dihydrobenzo-[c]thien-5-yl)acetyl]amino]-3-[[(5-methyl-1,3,4-thiadiazol-2-yl)thio]methyl]-8-oxo-5-thia-1-azabicyclo[4.2.0]-oct-2-ene-2-carboxylic acid $S^2$-oxide |

EXAMPLE 18

7-[[Amino(1,3-dihydrobenzo[c]thien-5-yl)acetyl]amino]-3-[[(1,3,4-thiadiazol-2-yl)thio]methyl]-8-oxo-5-thia-1-azabicyclo[4.2.0]oct-2-ene-2-carboxylic acid $S^2,S^2$-dioxide This procedure is based on the procedure described in J. Antibiotics, 23, 131 (1970). About 0.03 mole of 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide, about 0.03 mole of sodium bicarbonate and about 0.03 mole of (1,3,4-thiadiazol-2-yl)thiol are placed in 200 ml of a phosphate buffer, pH being about 6.5. The mixture is heated to about 60° C. for 5–7 hours. At the end of this time the pH is adjusted to about 4 to 6 by the addition of hydrochloric acid. The aqueous phase is extracted with ethyl acetate. The extract (ethyl acetate phase) is washed with sodium chloride and dried over magnesium sulfate. Evaporation of ethyl acetate gave a solid material, namely, 7-[[amino(1,3-dihydrobenzo[c]thien-5-yl)acetyl]amino]-3-[[(1,3,4-thiadiazol-2-yl)thio]methyl]-8-oxo-5-thia-1-azabicyclo[4.2.0]oct-2-ene-2-carboxylic acid $S^2,S^2$-dioxide.

Using the procedure of Example 18 and substituting the appropriate heterocyclic thiol for (1,3,4-thiadiazol-2-yl)thiol, the products shown below are prepared.

| 3-(ACETYLOXY)METHYL DERIVATIVE | THIOL HETEROCYCLE | PRODUCT |
|---|---|---|
| 3-[(acetyloxy)methyl]-7-[[amino-(1,3-dihydrobenzo(c)thien-5-yl)-acetyl]amino]-8-oxo-5-thia-1-azabicyclo[4.2.0]oct-2-ene-2-carboxylic acid $S^2,S^2$-dioxide | 5-methyl-1,3,4-thiadiazol-2-yl-thiol | 7-[[amino(1,3-dihydrobenzo[c]-thien-5-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid $S^2,S^2$-dioxide |
| 3-[(acetyloxy)methyl]-7-[[amino-(1,3-dihydrobenzo[c]thien-5-yl)-acetyl]amino]-7-methoxy-8-oxo-5-thia-1-azabicyclo[4.2.0]oct-2-ene-2-carboxylic acid $S^2,S^2$-dioxide | 1-methyltetrazol-5-yl-thiol | 7-[[amino(1,3-dihydrobenzo[c]-thien-5-yl)acetyl]amino]-7-methoxy-3-[[1-methyltetrazol-5-yl)thio]methyl]-8-oxo-5-thia-1-azabicyclo[4.2.0]oct-2-ene-2-carboxylic acid $S^2,S^2$-dioxide |
| 3-[(acetyloxy)methyl]-7-[[amino-(1,3-dihydrobenzo[c]thien-4-yl)-acetyl]amino]-8-oxo-5-thia-1-azabicyclo[4.2.0]oct-2-ene-2-carboxylic acid $S^2,S^2$-dioxide | 1,3,4-oxadiazol-2-yl-thiol | 7-[[amino(1,3-dihydrobenzo[c]-thien-4-yl)acetyl]amino]-3-[[(1,3,4-oxadiazol-2-yl)thio]methyl]-8-oxo-5-thia-1-azabicyclo[4.2.0]oct-2-ene-2-carboxylic acid $S^2,S^2$-dioxide |

| 3-(ACETYLOXY)METHYL DERIVATIVE | THIOL HETEROCYCLE | PRODUCT |
|---|---|---|
| 3-[(acetyloxy)methyl]-7-[[amino-(1,3-dihydrobenzo[c]thien-4-yl)-acetyl]amino]-7-methoxy-8-oxo-5-thia-1-azabicyclo[4.2.0]oct-2-ene-2-carboxylic acid $S^2,S^2$-dioxide | 1,3,4-triazol-2-ylthiol | 7-[[amino(1,3-dihydrobenzo[c]thien-4-yl)acetyl]amino]-7-methoxy-3-[[(1,3,4-triazol-2-yl)thio]methyl]-8-oxo-5-thia-1-azabicyclo[4.2.0]oct-2-ene-2-carboxylic acid $S^2,S^2$-dioxide |
| 3-[(acetyloxy)methyl]-7-[[amino-(1,3-dihydrobenzo[c]thien-5-yl)-acetyl]amino]-8-oxo-5-thia-1-azabicyclo[4.2.0]oct-2-ene-2-carboxylic acid $S^2$-oxide | 5-methyl-1,3,4-oxadiazol-2-ylthiol | 7-[[amino(1,3-dihydrobenzo[c]thien-5-yl)acetyl]amino]-3-[[(5-methyl-1,3,4-oxadiazol-2-yl)thio]methyl]-8-oxo-5-thia-1-azabicyclo[4.2.0]oct-2-ene-2-carboxylic acid $S^2$-oxide |
| 3-[(acetyloxy)methyl]-7-[[amino-(1,3-dihydrobenzo[c]thien-5-yl)-acetyl]amino]-8-oxo-5-thia-1-azabicyclo[4.2.0]oct-2-ene-2-carboxylic acid | 1-methyltetrazol-5-yl-thiol | 7-[[amino(1,3-dihydrobenzo[c]thien-5-yl)acetyl]amino]-3-[[(1-methyltetrazol-5-yl)thio]methyl]-8-oxo-5- thia-1-azabicyclo[4.2.0]oct-2-ene-2-carboxylic acid |

EXAMPLE 19

3-[(Acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide 2-amino-3-methyl butyryloxy methyl ester A suspension of 5 grams of 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide sodium salt and 8.5 grams of N-tert-butoxycarbonyl-L-valine chloromethyl ester, which is prepared by the general procedure described in W. German Offen. No. 2,236,620, are mixed in 100 ml of dimethylformamide and stirred for 72 hours. The mixture is diluted with ethyl acetate, washed with water and aqueous bicarbonate and again with water. The ethyl acetate portion is dried over magnesium sulfate, filtered and evaporated to dryness to give 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide N-tert-butoxycarbonyl-2-amino-3-methyl butyryloxymethyl ester from which the protecting group can be removed by standard procedures to give the title compound.

EXAMPLE 20

3-[(Acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic $S^2,S^2$-dioxide acid pivaloyloxy methyl ester The sodium salt of 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide (3 g) is added to about 40 ml of dry dimethylformamide (DMF) and stirred for about 30 minutes. Then 4.0 ml of chloromethylpivalate in 5 ml of DMF is added. This mixture is stirred for about 4 hours at room temperature. This mixture is diluted with ethyl acetate and thoroughly washed with water. The ethyl acetate portion is dried over sodium sulfate, filtered and evaporated to give 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide pivaloyloxymethyl ester.

In like manner, using sufficient quantities of chloromethylacetate, chloromethylpropionate, and chloromethylbutyrate, in place of the chloromethylpivalate, the following respective products are prepared:

3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide acetyloxymethyl ester;

3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide propionyloxymethyl ester; and 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide butyryloxymethyl ester.

EXAMPLE 21

3-[(Acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide p-(pivaloyloxy)benzyl ester 3-[(Acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide sodium salt, 6.6 mmole, is added to 35 ml of dimethylformamide (DMF) with stirring. Then 2 equivalents of p-(pivaloyloxy)benzyl alcohol is added and the mixture cooled to 0° C. To this is added 7.2 mmoles of dicyclohexylcarbodiimide in 7.5 ml of DMF. Stirring is continued at 0° C. for 1 hour and an additional 4 hours at room temperature. Filtration removes dicyclohexylurea formed in the reaction. The reaction mix is diluted with ethyl acetate, washed thoroughly with water and the organic phase is dried and filtered. Evaporation of the ethyl acetate gives 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide p-(pivaloyloxy)benzyl ester.

In like manner substituting sufficient quantities of p-(acetyloxy)benzyl alcohol, p-(propionyloxy)benzyl alcohol and p-(valeryloxy)benzyl alcohol for p-(pivaloxyloxy)benzyl alcohol, the respective compounds are produced:

3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide p-(acetyloxy)benzyl ester;

3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide p-(propionyloxy)benzyl ester; and 3-[(acetyloxy)methyl]-7-[[amino(1,3-dihydrobenzo[c]thien-5-yl)acetyl]amino]-8-oxo-5-thia-1-azabicyclo]4.2.0]oct-2-ene-2-carboxylic acid $S^2,S^2$-dioxide p-(valeroyloxy)benzyl ester.

EXAMPLE 22

3-[(Acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide N-ethoxycarbonyl-N-methylaminomethyl ester 725 mg (2.5 mM) of the sodium salt of 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide in 50 ml of dimethylformamide is treated at room temperature with 375 mg (2.5 mM) of N-chloromethyl-N-methylurethane for one hour. The mixture is carefully poured into ice water and the precipitated solid is removed by filtration and washed with water. The solid is dissolved in ethyl acetate and washed with aqueous sodium bicarbonate and then with water. The organic layer is dried over magnesium sulfate, filtered and evaporated to dryness in vacuo to give 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide N-ethoxycarbonyl-N-methylaminomethyl ester.

When in the above procedure an appropriate amount of N-methyl-N-propionylaminomethyl chloride, N-butyrylaminomethyl chloride, and N-acetylaminomethyl chloride is substituted for N-chloromethyl-N-methylurethane the following respective compounds are obtained:

3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide N-methyl-N-propionylaminomethyl ester;

3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide N-butyrylaminomethyl ester; and 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide N-acetylaminomethyl ester.

It is to be noted that the substituent group on the 7-amino group of the cephalosporin nucleus may be either amino(1,3-dihydrobenzo[c]thien-5-yl)acetyl or amino(1,3-dihydrobenzo[c]thien-4-yl)acetyl as exemplified in Examples 15, 16, 17 and 18.

EXAMPLE 23

D-α-Amino(1,3-dihydrobenzo[c]thien-5-yl)acetic acid

The resolving agent, binaphthyl phosphoric acid (BPA), is described in *Tetrahedron Letters,* 1971, 4617.

A racemic mixture of (D,L)-α-amino(1,3-dihydrobenzo[c]thien-5-yl)acetic acid is prepared according to the procedure in Example 7. The racemic mixture (14 mmole), is treated with (10 mmole) of (+)-binaphthyl phosphoric acid (BPA) and 4 mmole of hydrochloric acid in 25 ml of methanol. This mixture is refluxed for 30 minutes. After cooling to 0° C., the salt formed between (+)-BPA and D-α-amino(1,3-dihydrobenzo[c]thien-5-yl)acetic acid precipitates and is filtered.

The BPA-D-α-amino(1,3-dihydrobenzo[c]thien-5-yl)acetic acid salt (5.1 mmole) is slurried in 50 ml of methanol. Sodium acetate trihydrate (5.1 mmole) is added and the mixture is refluxed for 1 hour. The hot solution is filtered and the solid is washed with hot methanol to give D-α-amino(1,3-dihydrobenzo[c]thien-5-yl)acetic acid.

When in the above procedure the appropriate amounts of (D,L)-α-amino(1,3-dihydrobenzo[c]thien-5-yl)acetic acid 2-oxide, (D,L)-α-amino(1,3-dihydrobenzo[c]thien-5-yl)acetic acid, 2,2-dioxide; (D,L)-α-amino(1,3-dihydrobenzo[c]thien-4-yl)acetic acid; (D,L)-α-amino(1,3-dihydrobenzo[c]thien-4-yl)acetic acid, 2-oxide and (D,L)-α-amino(1,3-dihydrobenzo[c]thien-4-yl)acetic acid, 2,2-dioxide substituted for (D,L)-α-amino(1,3-dihydrobenzo[c]thien-5-yl)acetic acid gives the corresponding (D) isomers:

(D)-α-amino(1,3-dihydrobenzo[c]thien-5-yl)acetic acid 2-oxide;

(D)-α-amino(1,3-dihydrobenzo[c]thien-5-yl)acetic acid 2,2-dioxide;

(D)-α-amino(1,3-dihydrobenzo[c]thien-4-yl)acetic acid;

(D)-α-amino(1,3-dihydrobenzo[c]thien-4-yl)acetic acid 2-oxide; and (D)-α-amino(1,3-dihydrobenzo[c]thien-4-yl)acetic acid 2,2-dioxide.

A typical ointment can have the following composition

3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide

| Hydrophilic Base | 50 mg/g of ointment |
|---|---|
| Cetyl alcohol | 15% |
| White Wax | 1% |
| Sodium Lauryl sulfate | 2% |
| Propylene glycol | 10% |
| Water | 72% |

Add the cephalosporin derivative to a small amount of water and incorporate into the base such that 1 gram of the product contains 50 mg of the active cephalosporin derivative.

The daily dosage of the active ingredient may range from 1 mg to about 500 mg. The exact amount will vary with the patients size, age and type of infection.

A typical tablet can have the following composition:

7-[[amino(1,3-dihydrobenzo[c]thien-5-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid

| $S^2,S^2$-dioxide | 50 mg |
|---|---|
| Lactose, USP | 250 mg |
| Cornstarch, USP | 50 mg |
| Cornstarch, USP (as 10% starch paste) | 5 mg |
| Calcium Stearate | 2 mg |

The cephalosporin derivative, lactose and cornstarch are mixed and ground through a number 12 screen. The ground material is mixed with additional cornstarch as 10% starch paste and calcium stearate. Suitable size tablets can be prepared using a 5/16 inch diameter standard concave punch.

A typical parenteral solution may have the following composition:

3-[(Acetyloxy)methyl]-7-[[amino(1,3-

| | |
|---|---|
| dihydrobenzo[c]thien-5-yl)acetyl-]amino]-8-oxo-5-thia-1-azabicyclo[4.2.0]oct-2-ene-2-carboxylic acid $S^2,S^2$-dioxide | 1.0 g |
| White beeswax | 1.0 g |
| Peanut Oil, to make | 10.0 cc |

Melt wax into portion of the peanut oil and then add the remaining oil to the mix. Sterilize the mix at 150° C. for 2 hours with dry heat. Under sterile conditions mix the cephalosporin into the wax-oil mixture and place in an ampul and seal said ampul. For use, dilute contents of ampul with 10 cc of pure water and shake well. Each cc contains 50 mg of the cephalosporin compound.

The preferred compounds of this invention are those compounds represented by general formula 1 wherein n is 0, 1 or 2, $R_1$ and $R_2$ are hydrogen, $R_3$ is hydrogen, alkanoyloxy and heterocyclicthio and $R_4$ is hydrogen, and the 1,3-dihydrobenzo[c]thiophene ring is substituted at positions 4 and 5.

The more preferred are those compounds as represented by general formula 1 wherein n is 2, $R_1$, $R_2$ and $R_4$ are hydrogen, $R_3$ is hydrogen, alkanoyloxy or heterocyclicthio group and the substitution of the 1,3-dihydrobenzo[c]thiophene ring is at position 5.

I claim:

1. A compound selected from the formula

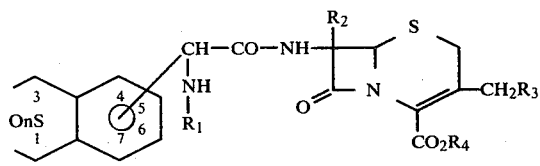

wherein n is 0, 1 or 2; $R_1$ is selected from the group consisting of hydrogen, a straight or branched lower alkanoyl group which has from 2 to 5 carbon atoms, and a straight or branched lower alkoxycarbonyl group in which the alkoxy portion has from 1 to 4 carbon atoms; $R_2$ is hydrogen or methoxy; $R_3$ is selected from the group consisting of hydrogen, a straight or branched lower alkanoyloxy group having 2 to 5 carbon atoms, 1,3,4-thiadiazol-2-ylthio, 5-methyl-1,3,4-thiadiazol-2-ylthio, tetrazol-5-ylthio, 1-methyltetrazol-5-ylthio, 1,3,4-oxadiazol-2-ylthio, 5-methyl-1,3,4-oxadiazol-2-ylthio, 1,3,4-triazol-2-ylthio, 5-methyl-1,3,4-triazol-2-ylthio and 1,2,3-triazol-5-ylthio; $R_4$ is selected from the group consisting of hydrogen, a straight or branched lower alkyl group of from 1 to 4 carbon atoms, an alkanoyloxymethyl group in which the alkanoyl portion is straight or branched and has from 2 to 5 carbon atoms, an alkanoylaminomethyl group in which the alkanoyl portion is straight or branched and has from 2 to 5 carbon atoms and the amine nitrogen is substituted with hydrogen or a straight or branched lower alkyl group having 1 to 4 carbon atoms, an alkoxycarbonylaminomethyl group in which the alkoxy portion is straight or branched and has from 1 to 4 carbon atoms and the amine nitrogen is substituted with hydrogen or a straight or branched lower alkyl group having 1 to 4 carbon atoms, a p-(alkanoyloxy)benzyl group in which the alkanoyl portion is straight or branched and has from 2 to 5 carbon atoms, and an aminoalkanoyloxymethyl group in which the alkanoyl portion has from 2 to 15 carbon atoms and the amino nitrogen is hydrogen substituted, or mono- or disubstituted with a straight or branched lower alkyl group having from 1 to 4 carbon atoms; or a pharmaceutically acceptable salt thereof.

2. A compound according to claim 1 wherein n is 2.

3. A compound according to claim 2 wherein substitution of the 1,3-dihydrobenzo[c]thiophene 2,2-dioxide ring system occurs at position 5.

4. A compound according to claim 3 wherein $R_1$ is hydrogen.

5. A compound according to claim 4 wherein $R_2$ is hydrogen.

6. A compound according to claim 4 wherein $R_2$ is methoxy.

7. A compound according to claim 2 wherein substitution of the 1,3-dihydrobenzo[c]thiophene 2,2-dioxide ring system occurs at position 4.

8. A compound according to claim 7 wherein $R_1$ is hydrogen.

9. A compound according to claim 8 wherein $R_2$ is hydrogen.

10. A compound according to claim 8 wherein $R_2$ is methoxy.

11. A compound of claim 1 of the formula

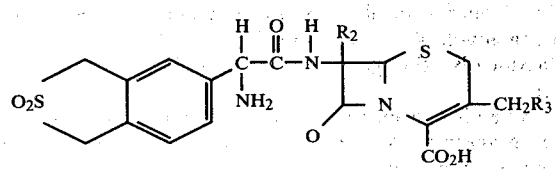

wherein $R_2$ is hydrogen or methoxy and $R_3$ is hydrogen, acetyloxy or (5-methyl-1,3,4-thiadiazol-2-yl)thio or a pharmaceutically acceptable salt thereof.

12. A compound according to claim 11 which is 7-[[amino(1,3-dihydrobenzo[c]thien-5-yl)acetyl]amino]-3-methyl-8-oxo-5-thia-1-azabicyclo[4.2.0]oct-2-ene-2-carboxylic acid $S^2,S^2$-dioxide or a pharmaceutically acceptable salt thereof.

13. A compound according to claim 11 which is 3-[(acetyloxy)methyl]-7-[[amino(1,3-dihydrobenzo[c]thien-5-yl)acetyl]amino]-8-oxo-5-thia-1-azabicyclo[4.2.0]oct-2-ene-2-carboxylic acid $S^2,S^2$-dioxide or a pharmaceutically acceptable salt thereof.

14. A compound according to claim 11 which is 7-[[amino(1,3-dihydrobenzo[c]thien-5-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid $S^2,S^2$-dioxide or a pharmaceutically acceptable salt thereof.

15. A compound according to claim 11 which is 7-[[amino(1,3-dihydrobenzo[c]thien-5-yl)acetyl]amino]-7-methoxy-3-methyl-8-oxo-5-thia-1-azabicyclo[4.2.0]oct-2-ene-2-carboxylic acid $S^2,S^2$-dioxide or a pharmaceutically acceptable salt thereof.

16. A compound according to claim 11 which is 3-[(acetyloxy)methyl]-7-[[amino(1,3-dihydrobenzo[c]thien-5-yl)acetyl]amino]-7-methoxy-8-oxo-5-thia-1-azabicyclo[4.2.0]oct-2-ene-2-carboxylic acid $S^2,S^2$-dioxide or a pharmaceutically acceptable salt thereof.

17. A compound according to claim 11 which is 7-[[amino(1,3-dihydrobenzo[c]thien-5-yl)acetyl]amino]-7-methoxy-3-[[(5-methyl-1,3,4-thiadiazol-2-yl)thio]methyl]-8-oxo-5-thia-1-azabicyclo[4.2.0]oct-2-ene-2-carboxylic acid $S^2,S^2$-dioxide or a pharmaceutically acceptable salt thereof.

18. A compound of claim 1 of the formula

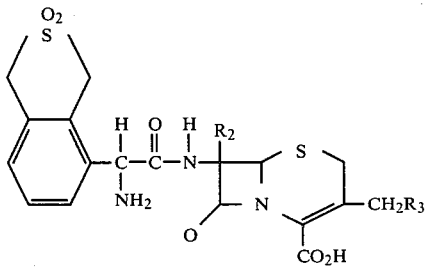

wherein $R_2$ is hydrogen or methoxy and $R_3$ is hydrogen, acetyloxy and 5-methyl-1,3,4-thiadiazol-2-yl or a pharmaceutically acceptable salt thereof.

19. A compound according to claim 18 which is 7-[[amino(1,3-dihydrobenzo[c]thien-4-yl)acetyl]amino]-3-methyl-8-oxo-5-thia-1-azabicyclo[4.2.0]oct-2-ene-2-carboxylic acid $S^2,S^2$-dioxide or a pharmaceutically acceptable salt thereof.

20. A compound according to claim 18 which is 3-[(acetyloxy)methyl]-7-[[amino(1,3-dihydrobenzo[c]thien-4-yl)acetyl]amino]-8-oxo-5-thia-1-azabicyclo[4.2.0]oct-2-ene-2-carboxylic acid $S^2,S^2$-dioxide or a pharmaceutically acceptable salt thereof.

21. A compound according to claim 18 which is 7--[[amino(1,3-dihydrobenzo[c]thien-4-yl)acetyl]amino]-3-[[(5-methyl-1,3,4-thiadiazol-2-yl)thio]methyl]-8-oxo-5-thia-1-azabicyclo[4.2.0]oct-2-ene-2-carboxylic acid $S^2,S^2$-dioxide or a pharmaceutically acceptable salt thereof.

22. A compound according to claim 18 which is 7-[[amino(1,3-dihydrobenzo[c]thien-4-yl)acetyl]amino]-7-methoxy-3-methyl-8-oxo-5-thia-1-azabicyclo[4.2.0]oct-2-ene-2-carboxylic acid $S^2,S^2$-dioxide or a pharmaceutically acceptable salt thereof.

23. A compound according to claim 18 which is 3-[(acetyloxy)methyl]-7-[[amino(1,3-dihydrobenzo[c]thien-4-yl)acetyl]amino]-7-methoxy-8-oxo-5-thia-1-azabicyclo[4.2.0]oct-2-ene-2-carboxylic acid $S^2,S^2$-dioxide or a pharmaceutically acceptable salt thereof.

24. A compound according to claim 18 which is 7-[[amino(1,3-dihydrobenzo[c]thien-4-yl)acetyl]amino]-7-methoxy-3-[[(5-methyl-1,3,4-thiadiazol-2-yl)thio]methyl]-8-oxo-5-thia-1-azabicyclo[4.2.0]oct-2-ene-2-carboxylic acid $S^2,S^2$-dioxide or a pharmaceutically acceptable salt thereof.

* * * * *